United States Patent [19]

Makisumi et al.

[11] Patent Number: 4,910,318

[45] Date of Patent: Mar. 20, 1990

[54] TETRAHYDROTHIOPYRANO(3,2-B)-INDOLE DERIVATIVES

[75] Inventors: Yasuo Makisumi, Hyogo; Takashi Sasatani, Nara, both of Japan

[73] Assignee: Shionogi & Co., Ltd., Osaka, Japan

[21] Appl. No.: 633,686

[22] Filed: Jul. 25, 1984

Related U.S. Application Data

[63] Continuation of Ser. No. 409,107, Aug. 18, 1982, abandoned, which is a continuation-in-part of Ser. No. 227,203, Jan. 22, 1981, abandoned.

[30] Foreign Application Priority Data

Feb. 27, 1980 [JP]  Japan .................................. 55-23751

[51] Int. Cl.[4] ........................................... C07D 495/02
[52] U.S. Cl. .................................................. 548/432
[58] Field of Search ....................... 548/430, 431, 432

[56] References Cited

PUBLICATIONS

Takada et al., "Studies on Fused Indoles I.", *Chem. Pharm. Bull.*, 32(3), 872–876, (1984).
Takada et al., "Studies on Fused Indoles II.", *Chem. Pharm. Bull.* 32(3), 877–886, (1984).

Primary Examiner—Donald G. Daus
Attorney, Agent, or Firm—Wenderoth, Lind & Ponack

[57] ABSTRACT

Tetrahydrothiopyrano[3,2-b]indole derivatives represented by the formula I:

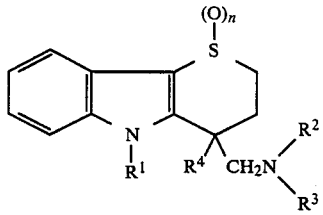

wherein
$R^1$ is hydrogen, $C_{1-4}$ alkyl, $C_{2-4}$ alkenyl, $C_{2-4}$ alkynyl, phenyl-$C_{1-4}$ alkyl, $C_{2-5}$ alkanoyl, or

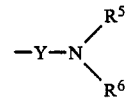

wherein Y is $C_{1-4}$ alkylene or $C_{1-4}$ oxoalkylene and $R^5$ and $R^6$ each is hydrogen or $C_{1-4}$ alkyl;
$R^2$ is hydrogen, $C_{1-4}$ alkyl or $C_{3-6}$ cycloalkyl;
$R^3$ is hydrogen, $C_{1-4}$ alkyl or

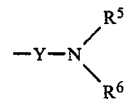

wherein Y, $R^5$ and $R^6$ each is as defined above;
or

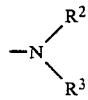

is pyrrolidino, piperdinyl, piperazinyl, 4-$C_{1-4}$ alkylpiperazinyl or morpholino;
$R^4$ is hydrogen or $C_{1-4}$ alkyl; and
n is 0 or an integer of 1 or 2
and the pharmaceutically acceptable salts being useful as analgesic and anti-inflammatory agents as well as psychoanaleptic and nootropic drug.

11 Claims, 1 Drawing Sheet

TETRAHYDROTHIOPYRANO(3,2-B)-INDOLE DERIVATIVES

This application is a Continuation of application Ser. No. 409,107 filed Aug. 18, 1982, now abandoned, which is a Continuation-In-Part of application Ser. No. 227,203 filed Jan. 22, 1981, now abandoned.

The present invention relates to novel tetradhydrothiopyrano[3,2-b]indole derivatives and pharmaceutically acceptable salts thereof and to a process for the preparation thereof.

The tetrahydrothiopyrano[3,2-b]indole derivatives and their pharmaceutically acceptable salts are useful medicaments exhibiting analgesic and anti-inflammatory activities. Additionally, they are useful as psychoanaleptic and nootropic drugs.

Tetradhydrothiopyrano[2,3-b]indole derivatives having a sulfur atom at the reversal position in the thiopyrane ring are already known to have analgesic and antiinflammatory activities (U.S. Pat. No. 4,256,640). Psychotropic activity for such compounds, however, has not been known. Additionally, the compounds decrease spontaneous locomotion and have hallucinogenic activity. There is little hope of the clinical application of the compounds because of these adverse side effects. On the contrary, the compounds of this invention moderately increase spontaneous locomotion and have no hallucinogenic activity. Furthermore, they have psychoanaleptic or nootropic activities. Accordingly, the present invention provides very valuable novel compounds.

Specifically, this invention provides a compound of the formula [I]:

wherein
$R^1$ is hydrogen, $C_{1-4}$ alkyl, $C_{2-4}$ alkenyl, $C_{2-4}$ alkynyl, phenyl-$C_{1-4}$ alkyl, $C_{2-5}$ alkanoyl, or wherein Y is $C_{1-4}$ alkylene or $C_{1-4}$ oxoalkylene and $R^5$ and $R^6$ each is hydrogen or $C_{1-4}$ alkyl;
$R^2$ is hydrogen, $C_{1-4}$ alkyl or $C_{3-6}$ cycloalkyl;
$R^3$ is hydrogen, $C_{1-4}$ alkyl or wherein Y, $R^5$ and $R^6$ each is as defined above; or is pyrrolidino, piperidinyl, piperazinyl, 4-$C_{1-4}$ alkylpiperazinyl or morpholino;
$R^4$ is hydrogen or $C_{1-4}$ alkyl; and
n is 0 or an integer of 1 or 2.

The following definitions are given for various terms used throughout this specification.

The term "$C_{1-4}$ alkyl" refers to straight and branched aliphatic radicals having from one to four carbon atoms including, e.g. methyl, ethyl, propyl, isopropyl, butyl, isobutyl, t-butyl and the like.

The term "$C_{2-4}$ alkenyl" refers to a group having one or more double bonds in the above straight or branched alkyl chain, e.g. vinyl, allyl, butenyl, isobutenyl and the like.

The term "$C_{2-4}$ alkynyl" refers to a group having one or more triple bonds in the above straight or branched alkyl chain including e.g. ethynyl, 1-propynyl, 2-propynyl, 2-butynyl and the like.

The term "$C_{3-6}$ cycloalkyl" includes cyclopropyl, cyclobutyl, cyclohexyl and the like. Additionally, $C_{2-5}$ alkanoyl includes e.g. acetyl, propionyl, butyryl, isobutyryl, valeryl and the like.

The group includes aminoalkyl, $C_{1-4}$ alkylaminoalkyl, N,N-di-$C_{1-4}$ alkylaminoalkyl and their oxo-substituted equivalents (e.g. aminomethyl, methylaminomethyl, isopropylaminomethyl, methylaminoethyl, ethylaminopropyl, N,N-dimethylaminomethyl, N,N-diethylaminoethyl, N,N-dimethylaminopropyl, carbamoyl, N-methylaminoacetyl and 3-(N,N-dimethylamino)-2-oxopropyl).

In the above definitions, the preferable $R^4$ is hydrogen and methyl; the most preferred is hydrogen. The preferably n is 0 and 1 and the most preferred is 0. The preferred $R^1$ is hydrogen and $C_{1-4}$ alkyl; methyl is the most preferred $R^1$. The prefered $R^2$ is hydrogen and $C_{1-4}$ alkyl, especially methyl and the preferred $R^3$ is $C_{1-4}$ alkyl, especially methyl and N,N-di-$C_{1-4}$ alkylaminoethyl, especially 2-N,N-diethylaminoethyl. The group is preferably N-$C_{1-4}$ alkylaminoethyl, N,N-di-($C_{1-4}$ alkyl)aminomethyl and N-$C_{1-4}$ alkyl-N-[2-N',N'-di-($C_{1-4}$ alkyl)aminoethyl]aminomethyl, especially methylaminomethyl, N,N-dimethylaminomethyl and N-methyl-N-(2-N', N'-diethylaminoethyl)aminomethyl, respectively; the most preferred group is methylaminomethyl.

The representative compounds of formula I are as follows:

Compounds of formula I wherein n is 0, $R^4$ is hydrogen,

1. $R^1$ and $R^2$ each is hydrogen and $R^3$ is methyl,
2. $R^1$ is hydogen and $R^2$ and $R^3$ each is methyl,
3. $R^1$ is hydrogen, $R^2$ is methyl and $R^3$ is 2-(N,N-diethyl-)aminoethyl,
4. $R^1$ is hydrogen and $R^2$ and $R^3$ taken together form piperadinyl,
5. $R^1$ is methyl, $R^2$ is hydrogen and $R^3$ is methyl,
6. $R^1$ is methyl, $R^2$ is hydrogen and $R^3$ is ethyl,
7. $R^1$ is methyl, $R^2$ is hydrogen and $R^3$ is isopropyl,
8. $R^1$ is methyl, $R^2$ is cyclohexyl and $R^3$ is hydrogen,
9. $R^1$, $R^2$ and $R^3$ each is methyl,
10. $R^1$ is methyl and $R^2$ and $R^3$ each is ethyl,
11. $R^1$ and $R^2$ each is methyl and $R^3$ is propyl,
12. $R^1$ and $R^2$ each is methyl and $R^3$ is 2-N,N-dimethylaminoethyl,
13. $R^1$ and $R^2$ each is methyl and $R^3$ is N,N-diethylcarbamoylmethyl,
14. $R^1$ and $R^2$ each is methyl and $R^3$ is methylaminomethyl,
15. $R^1$ is methyl and $R^2$ and $R^3$ taken together form pyrrolidino,
16. $R^1$ is methyl and $R^2$ and $R^3$ taken together form N-methylpiperazinyl,
17. $R^1$ is methyl and $R^2$ and $R^3$ taken together form morpholino,
18. $R^1$ is ethyl, $R^2$ is hydrogen and $R^3$ is methyl,
19. $R^1$ is ethyl, $R^2$ is hydrogen and $R^3$ is ethyl,
20. $R^1$ is ethyl, $R^2$ is hydrogen and $R^3$ is isopropyl,
21. $R^1$ is ethyl and $R^2$ and $R^3$ each is methyl,
22. $R^1$ is ethyl, $R^2$ is hydrogen and $R^3$ is 2-N,N-dimethylaminoethyl,
23. $R^1$ is ethyl, $R^2$ and $R^3$ taken together form piperidinyl,
24. $R^1$ is propyl, $R^2$ is hydrogen and $R^3$ is methyl,
25. $R^1$ is propyl and $R^2$ and $R^3$ each is methyl,
26. $R^1$ is propyl, $R^2$ is methyl and $R^3$ is 2-N,N-dimethylaminotrimethylene,
27. $R^1$ is propyl and $R^2$ and $R^3$ taken together form piperazinyl,
28. $R^1$ is isopropyl, $R^2$ is hydrogen and $R^3$ is methyl,
29. $R^1$ is isopropyl and $R^2$ and $R^3$ each is methyl,
30. $R^1$ butyl, $R^2$ is hydrogen and $R^3$ is methyl,
31. $R^1$ is butyl, $R^2$ is methyl and $R^3$ is 2-N,N-diethylaminoethyl,
32. $R^1$ is vinyl, $R^2$ is hydrogen and $R^3$ is methyl,
33. $R^1$ is allyl, $R^2$ is hydrogen and $R^3$ is methyl,
34. $R^1$ is allyl and $R^2$ and $R^3$ each is methyl,
35. $R^1$ is 2-propynyl, $R^2$ is hydrogen and $R^3$ is methyl,
36. $R^1$ is 2-propynyl and $R^2$ and $R^3$ each is methyl,
37. $R^1$ is 2-propynyl and $R^2$ and $R^3$ taken together form N-methylpiperazinyl,
38. $R^1$ is benzyl, $R^2$ is hydrogen and $R^3$ is methyl,
39. $R^1$ is benzyl and $R^2$ and $R^3$ each is methyl,
40. $R^1$ is acetyl, $R^2$ is hydrogen and $R^3$ is methyl,
41. $R^1$ is acetyl and $R^2$ and $R^3$ each is methyl,
42. $R^1$ is propionyl, $R^2$ is hydrogen and $R^3$ is methyl,
43. $R^1$ is propionyl and $R^2$ and $R^3$ each is methyl,
44. $R^1$ is N,N-diethylaminomethyl, $R^2$ is hydrogen and $R^3$ is methyl,
45. $R^1$ is 2-N-methylaminoethyl, $R^2$ is hydrogen and $R^3$ is methyl,
46. $R^1$ is 2-N,N-diethylaminoethyl, $R^2$ is hydrogen and $R^3$ is methyl,
47. $R^1$ is N-methylcarbamoylmethyl, $R^2$ is hydrogen and $R^3$ is methyl,
48. $R^1$ is N,N-diethylcarbamoylmethyl, $R^2$ is hydrogen and $R^3$ is methyl and
49. $R^1$ is N,N-diethylcarbamoylmethyl and $R^2$ and $R^3$ each is methyl; Compounds of formula I wherein n is 0, $R^4$ is methyl,
50. $R^1$ and $R^2$ each is hydrogen and $R^3$ is methyl,
51. $R^1$ is hydrogen and $R^2$ and $R^3$ each is methyl,
52. $R^1$ is methyl, $R^2$ is hydrogen and $R^3$ is methyl,
53. $R^1$ is methyl, $R^2$ is hydrogen and $R^3$ is ethyl,
54. $R^1$ is methyl, $R^2$ is hydrogen and $R^3$ is isopropyl,
55. $R^1$ and $R^2$ each is methyl and $R^3$ is 2-N,N-dimethylaminoethyl,
56. $R^1$ is ethyl, $R^2$ is hydrogen and $R^3$ is methyl,
57. $R^1$ is ethyl and $R^2$ and $R^3$ each is methyl,
58. $R^1$ is ethyl and $R^2$ and $R^3$ taken together form pyrrolidino,
59. $R^1$ is allyl, $R^2$ is hydrogen and $R^3$ is methyl; Compounds of formula I wherein n is 0, $R^4$ is ethyl,
60. $R^1$ is methyl, $R^2$ is hydrogen and $R^3$ is methyl,
61. $R^1$ is methyl and $R^2$ and $R^3$ each is ethyl; Compounds of formula I wherein n is 0, $R^4$ is propyl,
62. $R^1$, $R^2$ and $R^3$ each is methyl; Compounds of formula I wherein n is 1, $R^4$ is hydrogen,
63. $R^1$ is methyl, $R^2$ is hydrogen and $R^3$ is methyl,
64. $R^1$, $R^2$ and $R^3$ each is methyl,
65. $R^1$ is ethyl, $R^2$ is hydrogen and $R^3$ is methyl, and
66. $R^1$, $R^2$, and $R^3$ each is ethyl; Compounds of formula I wherein n is 1, $R^4$ is methyl;
67. $R^1$ is methyl, $R^2$ is hydrogen and $R^3$ is methyl, and
68. $R^1$, $R^2$ and $R^3$ each is methyl, Compounds of formula I wherein n is 2, $R^4$ is hydrogen,
69. $R^1$ is methyl, $R^2$ is hydrogen and $R^3$ is methyl,
70. $R^1$ is ethyl, $R^2$ is hydrogen and $R^3$ is methyl, and
71. $R^1$ is ethyl and $R^2$ and $R^3$ each is methyl and their salts.

The compound of this invention (hereinafter referred to as Compound [I]) includes 4-(substituted or unsubstituted-amino)methyl-2,3,4,5-tetrahydrothiopyrano[3,2-b]idoles optionally having a substituent at the 4 and/or 5 position, and the sulfur atom at the 1 position may be oxide or dioxide. Further, this invention includes the pharmaceutically acceptable salts of Compound [I], for example, hydrochloride, hydrobromide, hydroiodide, sulfate, phosphate, methanesulfonate, acetate, citrate, oxalate, fumarate, malate, succinate, maleate, phthalate, cinnamate, benzoate, ascorbate and the like.

Compound [I] is novel. A compound having the 2,3,4,5-tetrahydrothiopyrano[3,2-b]indole nucleus with any recognized pharmaceutical activity has not yet been known. Naturally, it is not known that Compound [I] has analgesic, anti-inflammatory and/or psychoanaleptic and nootropic activities.

Compound [I] can be prepared by various methods, one of which is illustrated as follows:

(wherein $R^1$, $R^2$, $R^3$, $R^4$ and n each is as defined above)

(1) Starting Compound [IV]

Thiol derivative [IV] is prepared by Harris's method: Tetrahedron Letters, 1969, 4465. Namely, indole or 1-substituted indole is treated with thiourea in the presence of iodine-potassium iodide and the resulting isothiuronium salt is hydrolyzed by alkali. Besides, 3-indolylthiol has been prepared by Harris and 1-methyl-3-indolylthiol by Marches: Chim. Ind. (Milan.), 51, 41 (1969).

(2) Process for preparing Compound [III] (Step (a))

Compound [III] is prepared by reacting Compound [IV] with 4-halogeno-2-butyn-1-ol in the presence of a dehydrohalogenating agent. The reaction is carried out in an inert organic solvent at room temperature or under heating.

(3) Process for preparing Compound II (Step (b))

Compound [II] can be prepared by cyclizing Compound [III] under heating. The reaction is carried out in an inert organic solvent (e.g. benzene, toluene, xylene, dimethylformamide, dimethylsulfoxide, alcohols, pyridine, dimethylaniline and the like).

(4) Process for preparing Compound [I]

Various routes can be taken to prepare Compound [I] from Compound [II] depending on the objective Compound [I]. A few typical methods are shown as follows:

a. Formation of aminomethyl or substituted aminomethyl group

The formyl group at the 4 position of Compound [II] can be converted into aminomethyl, for example, by reacting Compound [II] with ammonia or a primary or secondary amine under reductive conditions or followed by reduction, if necessary. The reaction of Compound [II] and an amine is carried out in an inert organic solvent, e.g. benzene, or alcohols, at room temperature or under heating. The resultant Schiff base is treated with a reducing agent such as metal hydride, sodium-alcohol, formic acid and the like. Formic acid is preferably used when a secondary amine is reacted. The reduction can proceed without isolation of the resultant Schiff base. Further, the reaction of Compound [II] can be effected with an amine under reaction conditions, namely in the presence of a suitable reducing agent to give the desired Compound [I].

b. Introduction of $R^4$

Alkylation of Compound [I] in which $R^4$ is hydrogen is effected in a usual manner and gives the objective Compound [I] in which $R^4$ is not hydrogen. There is exemplified an alkylation by using an alkali metal compound (e.g. sodium hydride, potassium hydroxide) and alkyl halide (e.g. methyl iodide) in an inert organic solvent (e.g. dimethylformamide, dioxane, dimethylsulfoxide).

c. Introduction and substitution of $R^1$ $R^1$ can be introduced into Compound [I] in which $R^1$ is hydrogen in the same manner as in the above b. Further, $R^1$ can be replaced by another desired $R^1$ by removing the former $R^1$ in a conventional manner followed by introducing another substituent $R^1$.

d. S-Oxidation

Oxidation of the sulfur atom at the 1 position (formation of sulfide and sulfoxide) can be carried out by a conventional method. The reaction is carried out with a conventional peracid (e.g. perchloric acid, periodic acid, perbenzoic acid, m-chloroperbenzoic acid) in an inert organic solvent at room temperature or under heating.

e. Other modification

Additionally to the above modification, a variety of modifications and substitutions may be effected by usual methods. Further, the product may be converted into the desired salt. The salt formation can be carried out in a conventional manner.

Besides, a reactive substituent of Compounds [I] and [II] may be protected at any step in the above steps a to e, if necessary, and the protecting group may be removed at a suitable step if required.

For example, nitrogen at the position 5 is protected with a suitable protecting group, for example, acyl (e.g. acetyl, trifluoroacetyl), alkoxyalkyl (e.g. methoxymethyl), benzyl and the like before an alkylamino or dialkylamino group is introduced into the formyl group at the position 4. The protecting group is removed in a usual manner, for example, with an acid when the protecting group is acyl or alkoxyalkyl and with sodium metal in liquid ammonia when the protecting group is benzyl after accomplishment of modification of the position 4.

On the contrary, the aminomethyl group at the position 4 may be protected during the modification of the nitrogen at the position 5. A common amino-protecting group, for example, acyl (e.g. acetyl, trifluoroacetyl), alkoxyalkyl (e.g. methoxymethyl) and t-butoxycarbonyl group may be used to protect the amino or imino group at the aminomethyl or N-mono substituted aminomethyl at the position 4. The protecting group is removed by the usual method, for example, with an acid (e.g. hydrochloric acid, sulfuric acid); trifluoroacetic acid is preferably used when the protecting group is a t-butoxycarbonyl group after completion of the modification of the nitrogen atom at position 5. The same protecting procedure is effected when Compound [I] is subjected to oxidation.

Some typical compounds of this invention were examined for physiological activities. The results are shown as follows:

1. Test Method (1) Anti-inflammatory activity (Carrageenin edema method)

A 0.9% saline solution (0.05 ml) containing 1.0% carrageenin is used as phlogistic agent. After 30 minutes JCl-Wistar female rats (180-200 g, body weight) are orally administered a test compound, the phlogistic agent is injected subcutaneously into the plantar of the feet of the rats. The volume of swelling is measured 3 hours later and the anti-edema activity is determined by calculating a ratio (%) of the edematous volume of medicated foot to that of non-medicated foot.

(2) Analgesic activity (Acetic acid writhing method)

DS male mice (20-23 g, body weight) are treated with an intraperitoneal injection of 0.1 ml/10 g of 0.6% acetic acid 30 minutes after oral administration of a test compound. The number of writhing times for 10 minutes is counted and $ED_{50}$ is calculated.

(3) Acute toxicity

DS mice (20-23 g, male) are orally administered a suspension of test compound with gum arabic. The mortality at the 72nd hour is determined and the $LD_{50}$ is calculated.

(4) Antidepressant activity (4)-a Anti-tetrabenazine ptosis test

Tetrabenazine (TBZ, 50 mg/kg s.c.) was administered to 5 mice for each group 1 hour after oral treatment with test compounds. Degree of the ptosis was measured 1 hour after TBZ administration according to the method of Janssen et al. (Arzneim.-Forsch./Drug Res. 15 104 (1965)). (4=complete, $3=\frac{3}{4}$, $2=\frac{1}{2}$, 1=4/1 closure of the eyelid, 0=normal).

(4)-b Anti-electroshock test with reserpine

Test compounds were administered (p.o.) 0.5 hour before reserpine (2.5 mg/kg s.c.) and the mice were subjected to minimal electroshock seizures according to the method of Swinyard et al. (J. Pharmacol. Exp. Ther. 106 319-330 (1952)). Seizures were induced by shocking mice (10 per dose) via a pair of corneal electrodes with current intensity of 12 mA and a duration of 0.2 sec 4 hours after administration of reserpine.

(5) Anti-cholinergic activity (Anti-oxotremorine hypothermia test)

Before each experiment the rectal temperature of the mice was recorded with a probe thermometer at a constant depth. The mice were divided into groups of 8 in such a way that the mean rectal temperature was the same in each group. Test compounds were administered orally 30 minutes before s.c. administration of oxotremorine (0.5 mg/kg).

(6) Spontaneous locomotor increasing activity

For each group 3 mice were used. Spontaneous locomotor activity was recorded for 15 minutes by a Varimex activity meter from 15 minutes after oral administration of a test compound. The $ED_{50}$ value was defined as the dose that resulted in 50% increase of the spontaneous locomotor activity compared to the control value.

(7) Spontaneous locomotor decreasing activity

For each group 5 mice were used. Spontaneous locomotor activity was recorded for 10 minutes by a Varimex activity meter from 60 minutes after oral administration of a test compound. The $ED_{50}$ value was defined as the dose that resulted in a 50% decrease of the spontaneous locomotor activity compared to the control.

(8) Hallucinogenic activity

Each of the five mice in each group was confined n a box for 15 minutes to let it adapt to its surroundings. The mouse was kept on a black disc of 74 cm in diameter for 2 minutes from 5 and 15 minutes after administration of a test compound. The number of bizarre behaviours (walking backwards, pivoting and the like) was counted.

2. Results

Figure 1:
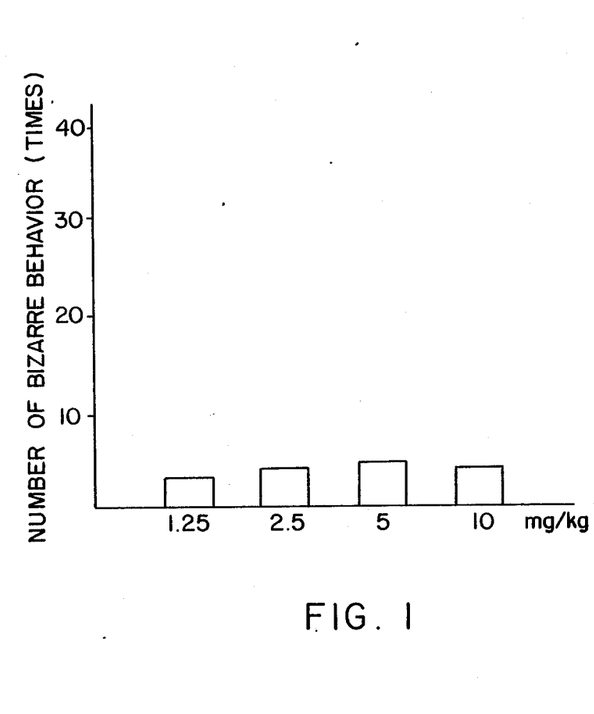
Figure 2:
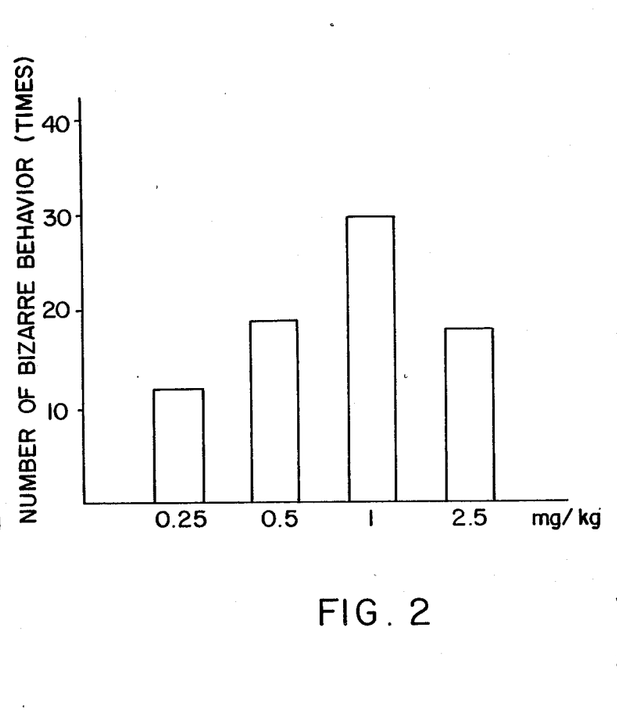

The results are shown in Tables 1-4 and FIGS. 1 and 2, wherein FIG. 1 shows the hallucinogenic activity of a compound of the present invention, and FIG. 2 shows the hallucinogenic activity of a reference compound.

TABLE 1

| Test Comp. No. | Structure[1] | | | | Addition salt | Test (1) $ED_{30}$ mg/kg | Test (2) $ED_{50}$ mg/kg | Test (3) $LD_{50}$ mg/kg |
| --- | --- | --- | --- | --- | --- | --- | --- | --- |
| | $R^1$ | $R^2$ | $R^3$ | n | | | | |
| 1 | Me[2] | Me | H | 0 | HCl | 9.4 | 6.4 | 400 |
| 2 | Et[3] | Me | H | 0 | Oxalate | 9.4 | 13.3 | 800 |
| 3 | Me | Me | Me | 0 | " | 28.3 | 17.8 | 400 |
| 4 | Me | Me | H | 1 | — | — | 49.0 | >1000[5] |
| 5 | $CH_2-CH=CH_2$ | Me | H | 0 | Oxalate | 17.5 | 11.3 | 700 |
| 6 | Me | Me | $CH_2CH_2N\genfrac{}{}{0pt}{}{Et}{Et}$ | 0 | " | 13.4 | 25.3 | 700 |
| Ref.[4] | | | | | HCl | — | 4.2 | 330 |
| Aminopyrine | | | | | | 24 | 58 | 800 |

Notes:

[1]

[2] Me = methyl
[3] Et = ethyl
[4] Ref. = 4-methylaminomethyl-2,3,4,9-tetrahydro-thiopyrano [3,2-b]indole HCl salt (a compound claimed in U.S. Pat. No. 4,256,640)
[5] ">1000" means that $LD_{50}$ value is more than 1000 mg/kg and the precise amount was not determined.

TABLE 2

| Anti-depressant and anti-cholinergic activities | | | |
|---|---|---|---|
| Test Item | Comp. 1 | Ref. | Imipramine |
| Anit-depressant Act. | | | |
| (4)-a Anti-tetrabenazine Ptosis M $ED_{50}$ | 24.4 | >50 | 6.0 |
| (4)-b Anti-electroshock with Reserpine M $ED_{50}$ | 4.3 | 8.4 | 101.6 |
| Anti-cholinergic Act. | | | |
| (5) Anti-oxotremorine hypothermia M $ED_{50}$ | >50 | >50 | 4.5 |

TABLE 3

| Increasing effects on spontaneous locomotion in mice | | | |
|---|---|---|---|
| Compound | Dose mg/kg | No. of groups | % of increase | $ED_{50}$ mg/kg (95% confidence limits) |
| Comp. 1 | 2.5 | 5 | (9.1) | |
|  | 5 | " | 54.3 | 5.6 |
|  | 10 | " | 91.4 | (4.89–6.27) |
|  | 20 | " | 123.0 | |
| Methamphetamine | 0.25 | 5 | (3.8) | |
|  | 0.5 | " | 45.4 | 0.6 |
|  | 1 | " | 62.5 | (0.48–0.74) |
|  | 2 | " | 137.8 | |

( ):inhibition

TABLE 4

| Decreasing effects on spontaneous locomotion in mice | | | |
|---|---|---|---|
| Compound | Dose mg/kg | No. of groups | % of decrease | $ED_{50}$ mg/kg (95% confidence limits) |
| Ref. | 25 | 5 | 7.4 | 43.0 |
|  | 50 | " | 75.3 | (36.6–49.7) |
|  | 100 | " | 97.2 | |
| Imipramine | 25 | 5 | 19.1 | 56.0 |
|  | 50 | " | 56.0 | |
|  | 100 | " | 62.9 | (47.2–78.4) |

As shown in Table 1, the above tested compounds have analgesic and anti-inflammatory activities. The analgesic activity is much stronger than a commercially available analgesic, aminopyrine.

Table 2 shows that Compound 1 has strong anti-depressant activity compared with an anti-depressant on the market, imipramine. Favourably, the compound of this invention has no anti-cholinergic acitivity.

Furthermore, Compound 1 moderately increases spontaneous locomotion in mice as shown in Table 3 although the reference compound in the prior art, U.S. Pat. No. 4,256,640 decreases the activity as shown in Table 4. Compound 1 does not have so strong increasing activity as methamphethamine, while continuous administration of Compound 1 maintains mild activity for more than 24 hours. The activity of methamphetamine continues only 2 to 3 hours even though by successive administration. Therefore, Compound 1 can be used as psychoanaleptic or nootropic drug having a mild and long lasting effect.

Favourably, Compound 1 has no hallucinogenic activity although the reference compound does as shown in FIGS. 1 and 2. Thus, Compound 1 can be used repeatedly for a long time as analgesic and anti-inflammatory agent as well as psychoanaleptic or nootropic drug.

The other compounds of this invention have nearly the same pharmacological acitivities. Accordingly, Compound [I] of this invention can be used as an analgesic and anti-inflammatory agent and a psychoanaleptic or nootropic drug.

Practically, Compound [I] and its pharmaceutically acceptable salts can be applied to treatment of various ailments, pains and mental diseases of humans and other animals.

The compounds of this invention can be administered along or in combination with pharmaceutically acceptable carriers and other drugs, if necessary, orally, percutaneously or by injection. Preferably, the compounds are used in combination with one or more carriers suited to the particular route of administration. Examples of solid carriers for internal or external use are lactose, sucrose, starch, dextrin, sodium bicarbonate, licorice powder, talc, kaoline, bentonite, calcium carbonate, paraffin and the like, and as gel or liquid carrier, gelatine, water, ethanol, isopropanol, chloroform, glycerol, and the like are exemplified.

Practical examples of suitable forms of pharmaceutical preparation of Compound [I] are tablets, capsules, pills, ointments, granules, powders, suppositories, aerosols and injectable solutions.

The invention also provides a therapeutic formulation which comprises 1 mg to 100 mg of one or more Compound [I] with or without a pharmaceutically acceptable carrier. Compound [I] is generally administered to human adults in an amount of about 5 to about 100 mg at a time, thought the amount may largely be varied depending on conditions, e.g. case history, age and sex of the patient, administration route and the like. The compound can be administered to humans either in a single or divided doses. The compound may also be administered at once for acute diseases. Thus, the invention includes a method for giving analgesic, psychoanaleptic and nootropic effects to an animal, which method comprises administering an effective amount of a Compound [I] to the animal.

The invention will now be further illustrated and described by way of the following examples. EXAMPLE 1

A-(1) 1-Ethyl-3-indolylthiol

A solution of 1-ethylindole (25 g) and thiourea (15.7 g) in methanol (400 ml) is mixed with an aqueous solution (250 ml) of potassium iodide (34.4 g) and iodine (26.3 g) and allowed to stand at room temperature for 2 hours. The mixture is stirred for 1 hour and condensed to give S-(1-ethyl-2-indolyl)isothiuronium iodide:mp. 225.5°–228° C. (decomp.). To the product is added 5% aqueous sodium hydroxide solution (200 ml). The mixture is heated at 90° C. for 10 minutes in argon atmosphere, washed with ether, acidified with a dilute hydrochloric acid and immediately extracted with ether. The extract is washed with water, dried and evaporated to give the title compound as a yellow oil: Yield 58.4%.

IR:$\nu_{max}^{CHCl_3}$ 2540 cm$^{-1}$.

NMR:$\delta_{CDCl_3}$ 1.35t(J=7, 3H) 2.82d(J=2, 1H, D$_2$O disappears) 4.02q(J=7, 2H).

A-(2) The same procedure as noted above gives 1-benzyl-3-indolylthiol.

Mp. 78°–80° C.

IR:$\nu_{max}^{CHCl_3}$ 2540 cm$^{-1}$.

NMR:$\delta_{CDCl_3}$ 2.90d(J=2, 1H, D$_2$O disappears) 5.25s(2H).

B-(1)    4-Formyl-5-methyl-2,3,4,5-tetrahydrothiopyrano[3,2-b]indole

After successive addition of 1-methyl-3-indolylthiol (15.5 g), 4-chloro-2-butyn-1-ol (8.72 g) and potassium carbonate (12.1 g) to acetone (300 ml), the mixture is stirred at room temperature in nitrogen atmosphere for 16 hours. The precipitate is filtered off and the filtrate is condensed at under 40° C. Diethylamine (5 ml) is added to the residue. The mixture is allowed to stand for 1 hour at room temperature and then water is added thereto, which is extracted with chloroform. The extract is dried and evaporated to dryness. The residue is applied to silica gel chromatography eluted with benzene/petroleum ether (4:1) and then benzene-benzene/ether (20:1). The latter fractions give 1-methyl-3-(4-hydroxy-2-butynylthio)indole (17.7 g) as yellow orange oil:Yield 78.4%.

IR:$\nu_{max}^{CHCl_3}$ 3600, 2210 cm$^{-1}$.

NMR:$\delta_{CDCl_3}$ 1.57brs(1H) 3.47t(J=2, 2H) 3.68s(3H) 4.18brt (2H).

$\delta_{d5-py}$ 3.50s(3H) 3.63t(J=2, 2H) 4.51t(J=2, 2H).

To dry toluene (200 ml) are added the above product (17.5 g) and dry pyridine (17.5 ml) and the mixture is refluxed for 15 hours in nitrogen atmosphere and evaporated to dryness. The residue is applied to column chromatography on silica gel eluted with benzene/petroleum ether (8:1) to give the title compound (13.3 g):mp. 100°–101° C.:Yield 76.0%. Recrystallization from benzene/petroleum benzine gives crystals melting at 100.5°–102° C.

IR:$\nu_{max}^{CHCl_3}$ 1730 cm$^{-1}$.

NMR:$\delta_{CDCl_3}$ 3.50s(3H) 3.76m(1H) 9.67d(J=2, 1H).

B-(2) The following compounds are obtained in the same procedure as described above.

4-Formyl-5-ethyl-2,3,4,5-tetrahydrothiopyrano[3,2-b]indole: a pale yellow oil.

IR:$\nu_{max}^{CHCl_3}$ 1720 cm$^{-1}$.

NMR:$\delta_{CDCl_3}$ 1.29t(J=7, 3H) 3.79m(1H) 4.07q(J=7, 2H) 9.96d(J=2, 1H).

4-Formyl-5-benzyl-2,3,4,5-tetrahydrothiopyrano[3,2-b]indole: mp. 88°–89° C.

IR:$\nu_{max}^{CHCl_3}$ 1725 cm$^{-1}$.

NMR:$\delta_{CDCl_3}$ 3.62m(1H) 5.62s(2H) 9.47d(J=2, 1H).

EXAMPLE 2

(1) 4-Methylaminomethyl-5-methyl-2,3,4,5-tetrahydrothiopyrano[3,2-b]indole

To a solution of 4-formyl-5-methyl-2,3,4,5-tetrahydrothiopyrano[3,2-b]indole (1.2 g) in benzene (12 ml) is added 10% solution (3.2 g) of methylamine in benzene. The mixture is stirred at room temperature for 2.5 hours and then evaporated to give 4-methyliminomethyl-5-methyl-2,3,4,5-tetrahydrothiopyrano[3,2-b]indole as an oil.

IR:$\nu_{max}^{CHCl_3}$ 1675 cm$^{-1}$.

NMR:$\delta_{CDCl_3}$ 3.25brs(3H) 3.60s(3H).

The above product is dissolved in methanol (15 ml) and sodium borohydride (138 mg) is added dropwise thereto with stirring under cooling. The mixture is allowed to stand at room temperature for 2 hours and evaporated to dryness. The residue is dissolved in chloroform, washed with water, dried and evaporated to give the title compound (1.16 g): Yield 90.8%. Recrystallization from benzene/petroleum benzine gives crystals melting at 125°–128° C.

NMR:$\delta_{CDCl_3}$ 2.40s(3H) 3.63s(3H).

Anal. Calcd. for $C_{14}H_{18}N_2S$:C, 68.25; H, 7.36; N, 11.37. Found: C, 68.56; H, 7.18; H, 11.54.

The above product is dissolved in acetone, and ether/hydrochloric acid is gradually added thereto.

The precipitated crystals are collected by filtration to give the hydrochloride: mp. 258°–250° C. (decomp.)

Anal. Calcd. for $C_{14}H_{19}N_2SCl$: C, 59.45; H, 6.77; N, 9.90. Found: C, 59.35; H, 6.87; N, 9.67.

(2) The same procedure as described above gives compound No. 2-2-2-9 in Table 5.

EXAMPLE 3

(1) 4-Dimethylaminomethyl-5-methyl-2,3,4,5-tetrahydrothiopyrano[3,2-b]indole

To 50% aqueous solution (610 mg) of dimethylamine are added 99% formic acid (575 mg) and benzene successively. The mixture is evaporated in order to remove the water by azeotropic distillation and then the benzene. A solution of 4-formyl-5-methyl-2,3,4,5-tetrahydrothiopyrano[3,2-b]indole (1.2 g) in benzene (15 ml) is added to the above residue dropwise over 10 minutes under heating. The mixture is refluxed for 5 hours, then made alkaline with sodium hydroxide under ice-cooling and extracted with ether. The extract is washed with a saline solution, dried and evaporated to give the title compound (780 mg): Yield 57.7%. Recrystallization from petroleum benzine gives crystals melting at 81°–83° C.

NMR: $\delta_{CDCl_3}$ 2.25s(6H) 3.55s(3H).

Anal. Calcd. for $C_{15}H_{20}N_2S$: C, 69.19; H, 7.74; N, 10.76. Found: C, 69.31; H, 7.73; N, 10.58.

Oxalate: mp. 228°–229.5° C. (decomp.).

(2) The same procedure as described above gives compound Nos. 3-2-3-6 in Table 5.

EXAMPLE 4

(1) 4-Methylaminomethyl-2,3,4,5-tetrahydrothiopyrano[3,2-b]indole

Liquid ammonia (ca. 100 ml) is trapped in a solution of 4-methylaminomethyl-5-benzyl-2,3,4,5-tetrahydrothiopyrano[3,2-b]indole (1.6 g) in ether (20 ml) under cooling at −70° C. A piece of sodium metal is added occasionally under refluxing. The refluxing is continued for 1.5 hours after the dark green color of the reaction mixture disappears. The reaction mixture is neutralized with ammonium chloride, the excess ammonia removed, and then the residue extracted with methylene chloride after addition of water. The extract is washed with water, dried and evaporated to give the title compound (1.06 g): Yield 91.4%. Recrystallization from benzene-petroleum benzine gives crystals melting at 100°–101° C.

IR: $\nu_{max}^{CHCl_3}$ 3460, 3300 cm$^{-1}$.

NMR: $\delta_{CDCl_3}$ 2.40s(3H) 10.13brs(1H).

Anal. Calcd. for $C_{13}H_{16}N_2S$: C, 67.20; H, 6.94; N, 12.06. Found: C, 67.29; H, 6.97; N, 11.70.

Hydrochloride: mp. 208°–217° C. (decomp.).

(2) The same procedure as described above gives the compound No. 4-2 in Table 5.

EXAMPLE 5

(1) 4-Dimethylaminomethyl-5-isopropyl-2,3,4,5-tetrahydrothiopyrano[3,2-b]indole

A solution of 4-dimethylaminomethyl-2,3,4,5-tetrahydrothiopyrano[3,2-b]indole (1.00 g) in dry dimethylformamide (25 ml) is mixed with 50% sodium hydride (293 mg) under stirring and the mixture is allowed to stand at 40° C. for 1 hour. Then, the reaction mixture is mixed with a solution of isopropyl iodide (1.63 g) in dimethylformamide (2 ml) and kept at 40° C. for 2 hours and further for 20 hours after addition of the reagent. The reaction mixture is mixed with ether and ice water successively at under 5° C. and the ether layer is separated. The aqueous layer is further extracted with ether. The combined ether layers are extracted with a dilute hydrochloric acid solution. The extract is made alkaline and extracted with methylene chloride. The extract is washed with water, dried and evaporated to give the title compound (910 mg) as an oil: Yield 77.8%.

NMR: $\delta_{CDCl_3}$ 1.52d(J=7) 1.66d(J=7) 2.27s(6H) 4.56m(J=7,1H).

Oxalate: mp. 135°–138° C. (decomp.).

Anal. Calcd. for $C_{19}H_{26}N_2O_4S$: C, 60.29; H, 6.92; N, 7.40. Found: C, 60.26; H, 6.86; N, 7.22.

(2) The same procedure as described above gives the compound Nos. 5-2 and 5-3 in Table 5.

EXAMPLE 6

(1) 4-Methylaminomethyl-5-isopropylaminomethyl-2,3,4,5-tetrahydrothiopyrano[3,2-b]indole (a) A solution of 4-methylaminomethyl-2,3,4,5-tetrahydrothiopyrano[3,2-b]indole (5.47 g) in dry tetrahydrofuran (50 ml) is mixed with triethylamine (3.58 g) and 2-t-butoxycarbonyloxyimino-2-phenylacetonitrile (5.93 g), allowed to stand at room temperature for 4 hours and evaporated to dryness. The residue is dissolved in methylene chloride and washed with a dilute sodium hydroxide solution. The solution is washed with water, dried and evaporated to dryness. The residue is applied to column chromatography on silica gel eluted with benzene/ether (20:1) to give 4-(N-methyl-N-t-butoxycarbonylaminomethyl)-2,3,4,5-tetrahydrothiopyrano[3,2-b]indole (5.33 g): Yield 68.2%. Recrystallization from benzene/petroleum benzine gives crystals melting at 151°–153° C. (decomp.).

(b) A solution of the above product (1.6 g) in dry dimethylformamide (15 ml) is mixed with 50% sodium hydride (300 mg) and heated at 40° C. for 1 hour. A solution of isopropyl iodide (1.64 g) in dimethylformamide (2 ml) is added thereto at 5° C. The mixture is kept at 40° C. for 20 hours and ether and ice water are successively added at under 5° C. The ether layer is separated and the aqueous layer is extracted with ether. The extract is combined with the ether layer, washed with a saline solution, dried and evaporated to give 4-(N-methyl-N-t-butoxycarbonylaminomethyl)-5-isopropyl-2,3,4,5-tetrahydrothiopyrano[3,2-b]indole as an oil.

IR: $\nu_{max}^{CHCl_3}$ 1680 cm$^{-1}$.

NMR: $\delta_{CDCl_3}$ 1.50s(9H) 1.54d(J=7) 1.71d(J=7) 2.93(3H) 4.67m(J=7, 1H).

The product is dissolved in dry methylene chloride (20 ml), mixed with trifluoroacetic acid (4 ml) at 10° C. under stirring and allowed to stand at room temperature for 2 hours. The solvent is evaporated at under 30° C. The residue is dissolved in methylene chloride, washed with a sodiumhydrogen carbonate solution and water successively at under 10° C., dried and evaporated to give the title compound (1.21 g) as a red oil: Yield 91.6%.

NMR: $\delta_{CDCl_3}$ 1.53d(J=7) 1.69d(J=7) 2.45s(3H) 4.60m(J=7, 1H).

Oxalate: mp. 183°–187° C. (decomp.).

Anal. Calcd. for $C_{18}H_{24}N_2O_4S$: C, 59.32; H, 6.64; N, 7.69. Found: C, 59.12; H, 6.59; N, 7.65.

(2) The same procedure as described above gives compound Nos. 6-2–6-6 in Table 5.

EXAMPLE 7

4-N-Methyl-N-(diethylcarbamoylmethyl)aminomethyl-5-methyl-2,3,4,5-tetrahydrothiopyrano[3,2-b]indole A solution of 4-methylaminomethyl-5-methyl-2,3,4,5-tetrahydrothiopyrano[3,2-b]indole (0.9 g) in tetrahydrofuran (30 ml) and dimethylformamide (5 ml) is mixed with triethylamine (740 mg) and a solution of N,N-diethylchloroacetamide (657 mg) in tetrahydrofuran (1 ml) is added dropwise thereto under ice cooling with stirring. The mixture is allowed to stand for 3 hours at room temperature and evaporated to dryness. After addition of water, the residue is extracted with chloroform. The chloroform layer is washed with water, dried and evaporated to give the title compound (1.26 g) as an oil: Yield 95.4%.

IR: $\nu_{max}^{CHCl_3}$ 1640 cm$^{-1}$.

NMR: $\delta_{CDCl_3}$ 2.42s(3H) 3.63s(3H) 4.01s(2H).

Oxalate: mp. 164°–167° C. (decomp.).

Anal. Calcd. for $C_{22}H_{31}N_3O_5S$: C, 58.78; H, 6.95; N, 9.35. Found: C, 58.83; H, 6.80; N, 9.12.

EXAMPLE 8

4-N-Methyl-N-(N,N-diethylaminoethyl)aminomethyl-5-methyl-2,3,4,5-tetrahydrothiopyrano[3,2-b]indole A solution of 4-N-methyl-N-(diethylcarbamoylmethyl)aminomethyl-5-methyl-2,3,4,5-tetrahydrothiopyrano[3,2-b]indole obtained in Example 7 in tetrahydrofuran is mixed with 3 moles lithium aluminium hydride and refluxed for 2 hours. The reaction mixture is poured into ice, made alkaline and extracted with chloroform. The extract is washed with water, dried and evaporated to give the title compound as an oil: Yield 91.1%.

NMR: $\delta_{CDCl_3}$ 1.00t(J=7, 6H) 2.30s(3H) 3.60s(3H).

Dioxalate: mp. 180.5°–184° C. (decomp.).

Anal. Calcd. for $C_{24}H_{35}N_3O_8S$: C, 54.84; H, 6.71; N, 7.99. Found: C, 54.97; H, 6.47; N, 8.09.

EXAMPLE 9

(1) 4-Formyl-4,5-dimethyl-2,3,4,5-tetrahydrothiopyrano[3,2-b]indole

A solution of 4-formyl-5-methyl-2,3,4,5-tetrahydrothiopyrano[3,2-b]indole (2.31 g) in dry tetrahydrofuran (25 ml) is mixed with 50% sodium hydride (480 mg) and stirred at room temperature for 1.5 hours. Under ice cooling, a solution of methyl iodide (1.7 g) in dry tetrahydrofuran (5 ml) is added dropwise thereto over 5 minutes. The mixture is stirred further for 1.5 hours at room temperature and poured into ice water, which is extracted with ether. The extract is washed with water, dried and evaporated to dryness. The residue is applied to liquid chromatography eluted with benzene/hexane (5:1) to give the title compound (1.62 g): Yield 66.2%.

Mp. 119°–123° C.

(2) The same procedure as described above gives 4-formyl-4-methyl-5-ethyl-2,3,4,5-tetrahydrothiopyrano[3,2-b]indole.

Mp. 88.5°–90° C.

IR: $\nu_{max}^{CHCl_3}$ 1720 cm$^{-1}$.

NMR: $\delta_{CDCl_3}$ 1.28t(J=7, 3H) 1.53s(3H) 3.99q(J=7, 2H) 9.57s(1H).

EXAMPLE 10

(1) 4-Methylaminomethyl-4,5-dimethyl-2,3,4,5-tetrahydrothiopyrano[3,2-b]indole

In the same procedure as described in Example 2, 4-formyl-4,5-dimethyl-2,3,4,5-tetrahydrothiopyrano[3,2-b]indole is allowed to react with methylamine to give the title compound: Yield 97.4%.

NMR: $\delta_{CDCl_3}$ 0.72brs(1H) 1.38s(3H) 2.37s(3H) 3.80(3H).

Hydrochloride: mp. 222°–225° C.

Anal. Calcd. for: $C_{15}H_{21}N_2SCl$: C, 60.69; H, 7.13; N, 9.44. Found: C, 60.54; H, 7.46; N, 9.39.

(2) The same procedure as described above gives compound Nos. 10-2–10-6 in Table 5.

EXAMPLE 11

4-N-Dimethylaminomethyl-4,5-dimethyl-2,3,4,5-tetrahydrothiopyrano[3,2-b]indole

In the same procedure as in Example 3, 4-formyl-4,5-dimethyl-2,3,4,5-tetrahydrothiopyrano[3,2-b]indole is allowed to react with dimethylamine to give the title compound as an oil: Yield 31.3%.

NMR: $\delta_{CDCl_3}$ 1.40s(3H), 2.10s(6H) 3.83s(3H).

Oxalate: mp. 168°–171° C. (decomp.).

Anal. Calcd. for $C_{18}H_{26}N_2O_5S$: C, 56.53; H, 6.85; N, 7.32 S, 8.38. Found: C, 56.61; H, 6.55; N, 7.04; S, 8.51.

EXAMPLE 12

4-Methylaminomethyl-5-ethyl-2,3,4,5-tetrahydrothiopyrano[3,2-b]indole 1-oxide

A solution of 4-methylaminomethyl-5-ethyl-2,3,4,5-tetrahydrothiopyrano[3,2-b]indole (1.3 g) in methanol (30 ml) is mixed with an aqueous solution (10 ml) of sodium periodide (1.12 g) and kept at room temperature for 5 hours. The precipitate is filtered off and the filtrate is condensed. The residue is dissolved in methylene chloride, washed with water, dried and evaporated to give the title compound (1.28 g) as an oil: Yield 92.8%.

IR: $\nu_{max}^{CHCl_3}$ 1010 cm$^{-1}$.

NMR: $\delta_{CDCl_3}$ 1.35t(J=7, 3H) 2.41s(3H) 4.17q(J=7, 2H).

Oxalate: mp. 213°–217° C. (decomp.).

Anal. Calcd. for $C_{17}H_{22}N_2O_5S$: C, 55.72; H, 6.05; N, 7.64 S, 8.75. Found: C, 55.54; H, 6.07; N, 7.54 S, 8.61.

EXAMPLE 13

(1) 4-Methylaminomethyl-5-methyl-2,3,4,5-tetrahydrothiopyrano[3,2-b]indole 1-oxide (a) A solution of 4-methylaminomethyl-5-methyl-2,3,4,5-tetrahydrothiopyrano[3,2-b]indole (3.2 g) in dry tetrahydrofuran (30 ml) is allowed to react with triethylamine and 2-t-butoxycarbonyloxyimino-2-phenylacetonitrile in the same manner as in Example 6(a) to give 4-(N-methyl-N-t-butoxycarbonylaminomethyl)-5-methyl-2,3,4,5-tetrahydrothiopyrano[3,2-b]indole: Yield 87.0%. Mp. 111.5°–114° C. (decomp.) (b) The above product is treated in the same procedure as in Example 12 to give 4-(N-methyl-N-t-butoxycarbonylaminomethyl)-5-methyl-2,3,4,5-tetrahydrothiopyrano[3,2-b]indole 1-oxide. Mp. 218°–220.5° C. (decomp.). The product is dissolved in methylene chloride (20 ml) and trifluoroacetic acid (4 ml) is added thereto. The mixture is kept at room temperature for 2 hours and then treated in the usual manner to give the title compound (1.13 g): Yield 89.7%.

Mp. 208°–212° C.

IR: $\nu_{max}^{CHCl_3}$ 1010 cm$^{-1}$.

NMR: $\delta_{CDCl_3}$ 1.41brs(1H) 2.48s(3H) 3.72s(3H).

Anal. Calcd. for $C_{14}H_{18}N_2OS$: C, 64.09; H, 6.91; N, 10.68. Found: C, 64.05; H, 6.93; N, 10.46.

(2) 4-Methylaminomethyl-5-methyl-2,3,4,5-tetrahydrothiopyrano[3,2-b]indole 1,1-dioxide A solution of 4-(N-methyl-N-t-butoxycarbonylaminomethyl)-5-methyl-2,3,4,5-tetrahydrothiopyrano[3,2-b]indole (1.7 g) obtained in above (1) (a) in chloroform (20 ml) is mixed with a solution of m-chloroperbenzoic acid (2.37 g) in chloroform (30 ml) under ice-cooling with stirring and the mixture is kept at room temperature for 3 hours. The reaction mixture is washed with a sodium hydroxide aqueous solution and water, dried and evaporated to give 4-(N-methyl-N-t-butoxycarbonylaminomethyl)-5-methyl-2,3,4,5-tetrahydrothiopyrano[3,2-b]indole 1,1-dioxide.

Mp. 222°–224.5° C. (decomp.).

The above product is treated with trifluoroacetic acid in the same manner as in the above (1) (b) to give the title compound (880 mg): Yield 64.7%.

Mp. 170°–175° C.

IR: $\nu_{max}^{CHCl_3}$ 1280, 1130 cm$^{-1}$.

NMR: $\delta_{CDCl_3}$ 1.33brs(1H) 2.47s(3H) 3.73s(3H).

Anal. Calcd. for $C_{14}H_{18}N_2O_2S$: C, 60.41; H, 6.52; N, 10.06. C, 60.61; H, 6.52; N, 9.72.

TABLE 5

![Structure with R1, R2, R3 substituents on thiophene-fused bicyclic with CH2N(R2)(R3) group]

| Comp. No. | Substituent R¹ | R² | R³ | Yield (%) | NMR: $\delta_{CDCl_3}$ or IR: $\nu_{CHCl_3}$ cm$^{-1}$ | mp¹ (°C) | Experimental Analysis Formula: Calculated: Found: C H N Cl S |
|---|---|---|---|---|---|---|---|
| 2-2 | Me | Et | H | 91.9 | 1.08t(J=7, 3H) 3.65s (3H) | Oxalate 230–233(d) | $C_{15}H_{20}N_2S\cdot C_2H_2O_4$ 58.27 6.33 7.99 58.08 6.26 7.91 |
| 2-3 | Me | i-Pr | H | 93.1 | 1.07d(J=7, 6H) 3.65s (3H) | Oxalate 220–224(d) | $C_{16}H_{22}N_2S\cdot C_2H_2O_4$ 59.32 6.64 7.69 59.38 6.46 7.45 |
| 2-4 | Me | ![cyclohexyl-H] | H | 91.8 | 3.60s(3H) | HCl salt 239–243(d) | $C_{19}H_{26}N_2S\cdot HCl$ 65.03 7.55 7.98 10.10 64.86 7.77 7.93 10.36 |
| 2-5 | Et | Me | H | 94.9 | 1.28t(J=7, 3H) 2.41s (3H) 4.12q(J=7, 2H) | Oxalate 208–210.5(d) | $C_{15}H_{20}N_2S\cdot C_2H_2O_4$ 58.27 6.33 7.99 57.96 6.33 7.83 |
| 2-6 | Et | Et | H | 95.5 | 4.13q(J=7, 2H) | Oxalate 210–213.5(d) | — |
| 2-7 | Et | i-Pr | H | 95.0 | 1.08d(J=6, 6H) 1.33t(J=7, 3H) | Oxalate 189–193(d) | $C_{17}H_{24}N_2S\cdot C_2H_2O_4$ 60.29 6.92 7.40 60.23 6.94 7.36 |
| 2-8 | CH₂Ph | Me | H | 95.3 | 1.50brs(1H) 2.25s(3H) 5.30s(2H) | HCl salt 209–213(d) | $C_{20}H_{22}N_2S\cdot HCl$ 66.93 6.46 7.80 66.64 6.45 7.70 |
| 2-9 | Et | H | CH₂CH₂N(Me)(Me) | 94.2 | 1.23t(J=7, 3H) 2.15s(6H) 4.08q(2H) | Dioxalate 207–210 | $C_{18}H_{27}N_3S\cdot 2C_2H_2O_4$ 53.11 6.28 8.45 52.84 6.45 8.17 |
| 3-2 | Me | Et | Et | 84.5 | 0.96t(J=7, 6H) 3.53s (3H) | 93–95 | $C_{17}H_{24}N_2S$ 70.79 8.39 9.71 70.65 8.36 9.57 |
| 3-3 | Me | ![N-CH3 piperidine] | | 64.5 | 2.27s(3H) 3.63s(3H) | — | $C_{18}H_{25}N_3S\cdot 2HCl\cdot H_2O$ 53.20 7.19 10.34 53.22 7.31 10.05 |

TABLE 5-continued

[Structure: benzene ring connected to N-R¹ and to C=S, with S attached to a cyclohexene ring bearing CH₂N(R²)(R³)]

| Comp. No. | Substituent R¹ | R² | R³ | Yield (%) | NMR: $\delta_{CDCl_3}$ or IR: $\nu_{CHCl_3}$ cm⁻¹ | mp (°C.) | Experimental Analysis Formula: Calculated: Found: C H N Cl S |
|---|---|---|---|---|---|---|---|
| 3-4 | Et | Me | Me | 82.1 | 1.35t(J=7, 3H) 2.30s (6H) 4.15q(J=7, 2H) | 67–69 | $C_{16}H_{22}N_2S$ 70.03 8.08 10.21 / 69.89 8.05 10.00 |
| 3-5 | Et | Et | (cyclohexane ring) | 94.5 | 12.5t(J=7, 3H) | 121.5–124 | $C_{19}H_{26}N_2S$ 72.56 8.33 8.91 / 72.32 8.25 8.61 |
| 3-6 | CH₂Ph | Me | Me | 63 | 2.17s(6H) 5.36s(2H) | — | — |
| 4-2 | H | Me | Me | 93.5 | 2.32s(6H) 10.26brs(1H) | 138.5–139.5 | $C_{14}H_{18}N_2S$ 68.25 7.36 11.37 / 68.31 7.36 11.11 |
| 5-2 | COCH₃ | Me | Me | 92 | 2.27s(6H) 2.68s(3H) 3.97m(1H) IR: $\nu_{CHCl_3}$ 1690 cm⁻¹ | Oxalate 176–179 | $C_{16}H_{18}N_2OS \cdot C_2O_4H_2$ 57.13 5.86 7.40 / 56.81 5.86 7.11 |
| 5-3 | COC₂H₅ | Me | Me | 91.9 | 1.36t(J=7, 3H) 2.30s (6H) 4.03m(1H) IR: $\nu_{CHCl_3}$ 1690 cm⁻¹ | HCl salt 242–246(d) | $C_{17}H_{22}N_2OS \cdot HCl$ 60.24 6.84 8.27 / 60.07 6.89 8.04 |
| 6-2 | CH₂CH=CH₂ | Me | H | 91.3 | 1.35brs(1H) 2.43s(3H) 1640, 980, IR: $\nu_{CHCl_3}$ 915 cm⁻¹ | Oxalate 185–188.5(d) | $C_{16}H_{20}N_2S \cdot C_2O_4H_2$ 59.65 6.12 7.73 / 60.01 6.23 7.56 |
| 6-3 | CH₂C≡CH | Me | H | 100 | 2.43s(3H) 2.22(J=2, 1H) 4.83d(J=2, 2H) IR: $\nu_{CHCl_3}$ 3300, 2110 cm⁻¹ | HCl salt 218–221(d) | $C_{16}H_{18}N_2S \cdot HCl$ 62.63 6.24 9.13 / 62.68 6.22 8.82 |
| 6-4 | COCH₃ | Me | H | 67.9 | 2.15s(3H) 3.30s(3H) IR: $\nu_{CHCl_3}$ 1630 cm⁻¹ | 186–189 | $C_{15}H_{18}N_2OS$ 65.66 6.61 10.21 / 66.09 6.67 10.04 |
| 6-5 | CH₂CON(Et)(Et) | Me | H | 100 | 1.60brs(1H) 2.39s(3H) 4.95s(2H) IR: $\nu_{CHCl_3}$ 1650 cm⁻¹ | 131–133.5 | $C_{19}H_{27}N_3OS$ 66.05 7.88 12.16 / 65.79 7.76 12.37 |
| 6-6 | CH₂CH₂N(Me)(Me) | Me | H | 93.6 | 1.40brs(1H) 2.28s(6H) 2.44s(3H) 4.18m(2H) | 2HCl salt 268–270(d) | $C_{17}H_{25}N_3S \cdot 2HCl$ 54.25 7.23 11.16 18.83 / 53.99 7.15 10.89 18.55 |
| 10-2³ | Me | Et | H | 97.0 | 0.60brs(1H) 1.00t(J=7, ...) | HCl salt | $C_{16}H_{22}N_2S \cdot HCl$ 11.69 / 11.40 |

TABLE 5-continued

[Structure shown: benzothiophene fused bicyclic with N-R¹ and CH₂N(R²)(R³) substituents]

| Comp. No. | Substituent R¹ | Substituent R² | Substituent R³ | Yield (%) | NMR: $\delta_{CDCl_3}$ or IR: $\nu_{CHCl_3}$ cm$^{-1}$ | mp[1] (°C.) | Experimental Analysis Formula: Calculated: Found: C H N Cl S |
|---|---|---|---|---|---|---|---|
| | | | | | 3H) 1.36(3H) 3.77s(3H) | 236-240 | 61.82 7.46 9.01<br>61.60 7.46 8.89 |
| 10-3[3] | Me | i-Pr[4] | H | 96.1 | 0.60brs(1H)<br>0.95d 0.98d(J=6, 6H)<br>1.37s(3H) 3.77s(3H) | HCl salt 227-229.5 | C₁₇H₂₄N₂S.HCl<br>62.84 7.76 8.62<br>62.70 7.77 8.54 |
| 10-4[3] | Me | CH₂CH₂N(Me)(Me) | H | 96.9 | 1.26brs(1H) 1.38s(3H)<br>2.13(6H) 3.77s(3H) | Dioxalate 219-222 | C₁₈H₂₇N₃S.2C₂H₂O₄<br>53.11 6.28 8.45<br>52.94 6.52 8.18 |
| 10-5[3] | Et | Me | H | 95.0 | 0.75brs(1H)<br>1.33t 1.39s(3H)<br>2.35s(3H) 4.30q(J=7, 5H) | HCl salt 194-198 | C₁₆H₂₂N₂S.HCl<br>61.82 7.46 9.01<br>62.06 7.47 8.81 |
| 10-6[3] | Et | Et | H | 90.9 | 0.83brs(1H)<br>0.98t(J=7, 3H) 1.30t<br>(J=7, 3H) 1.37s(3H) | HCl salt 203-206 | C₁₆H₂₄N₂S.HCl<br>62.84 7.76 8.62<br>62.71 7.73 8.68 |

Notes:
[1]d = decomposition,
[2]Cyclohexyl,
[3]The compound is substituted by methyl at the 4 position.
[4]Isopropyl.

What we claim is:

1. A compound of the formula:

wherein $R^1$ is $C_{1-3}$ alkyl and $R^2$ is $C_{1-3}$ alkyl, or a pharmaceutically acceptable salt of said compound.

2. A compound claimed in claim 1 wherein $R^1$ is methyl.

3. A compound claimed in claim 1 wherein $R^2$ is methyl.

4. The compound claimed in claim 1 which is 4-methylaminomethyl-5-methyl-2,3,4,5-tetrahydrothiopyrano[3,2-b]indole.

5. The compound claimed in claim 1 which is 4-methylaminomethyl-5-ethyl-2,3,4,5-tetrahydrothiopyrano[3,2-b]indole.

6. The compound claimed in claim 1 which is 4-ethylaminomethyl-5-methyl-2,3,4,5-tetrahydrothiopyrano[3,2-b]indole.

7. The compound claimed in claim 1 which is 4-isopropylaminomethyl-5-methyl-2,3,4,5-tetrahydrothiopyrano[3,2-b]indole.

8. The compound claimed in claim 1 which is 4-ethylaminomethyl-5-ethyl-2,3,4,5-tetrahydrothiopyrano[3,2-b]indole.

9. The compound claimed in claim 1 which is 4-isopropylaminomethyl-5-ethyl-2,3,4,5-tetrahydrothiopyrano[3,2-b]indole.

10. The compound claimed in claim 1 which is 4-methylaminomethyl-5-propyl-2,3,4,5-tetrahydrothiopyrano[3,2-b]indole.

11. The compound claimed in claim 1 which is 4-methylaminomethyl-5-isopropyl-2,3,4,5-tetrahydrothiopyrano[3,2-b]indole.

* * * * *